United States Patent
Benchetrit (12)

(10) Patent No.: US 6,171,330 B1
(45) Date of Patent: Jan. 9, 2001

(54) PNEUMATIC SURGICAL INSTRUMENT FOR THE DISTRIBUTION AND PLACEMENT OF CONNECTING OR FASTENING MEANS

(75) Inventor: Salomon Benchetrit, Caluire (FR)

(73) Assignee: Sofradim Production, Trevoux (FR)

( * ) Notice: Under 35 U.S.C. 154(b), the term of this patent shall be extended for 0 days.

(21) Appl. No.: 09/331,046

(22) PCT Filed: Dec. 15, 1997

(86) PCT No.: PCT/IB97/01566

§ 371 Date: Jul. 12, 1999

§ 102(e) Date: Jul. 12, 1999

(87) PCT Pub. No.: WO98/26718

PCT Pub. Date: Jun. 25, 1998

(51) Int. Cl.⁷ ................................................. A61B 17/08
(52) U.S. Cl. .......................................................... 606/219
(58) Field of Search ............................ 606/219, 75, 217; 227/19, 121, 120

(56) References Cited

U.S. PATENT DOCUMENTS 4,569,469 * 2/1986 Mongeon et al. ...................... 606/75
4,943,294 7/1990 Knapp .
5,257,632 11/1993 Turkel et al. .

FOREIGN PATENT DOCUMENTS

| 0 041 022 A1 | 12/1981 | (EP) . | |
|---|---|---|---|
| 0085931 | * 2/1983 | (EP) | ...................................... 227/19 |
| 0 085 931 A2 | 8/1983 | (EP) . | |
| 0 182 418 A2 | 8/1986 | (EP) . | |
| 1 328 841 | 9/1973 | (GB) . | |

* cited by examiner

*Primary Examiner*—Michael Buiz
*Assistant Examiner*—Tan-Uyen Thi Ho
(74) *Attorney, Agent, or Firm*—Oliff & Berridge, PLC

(57) ABSTRACT

The handle body (A) constitutes one of the branches of a T, of which the other branch is formed by its attachment piece (2) which is continued by the interchangeable element (B), and this body includes, on the side toward the interchangeable element (B), indentations (26) for positioning the fingers of the hand, said indentations (26) being arranged on either side of the attachment piece, and of which one (26a), for positioning the index finger, is equipped with a bore through which there protrudes the push-button (14) for activating the pneumatic distributor (11).

9 Claims, 3 Drawing Sheets

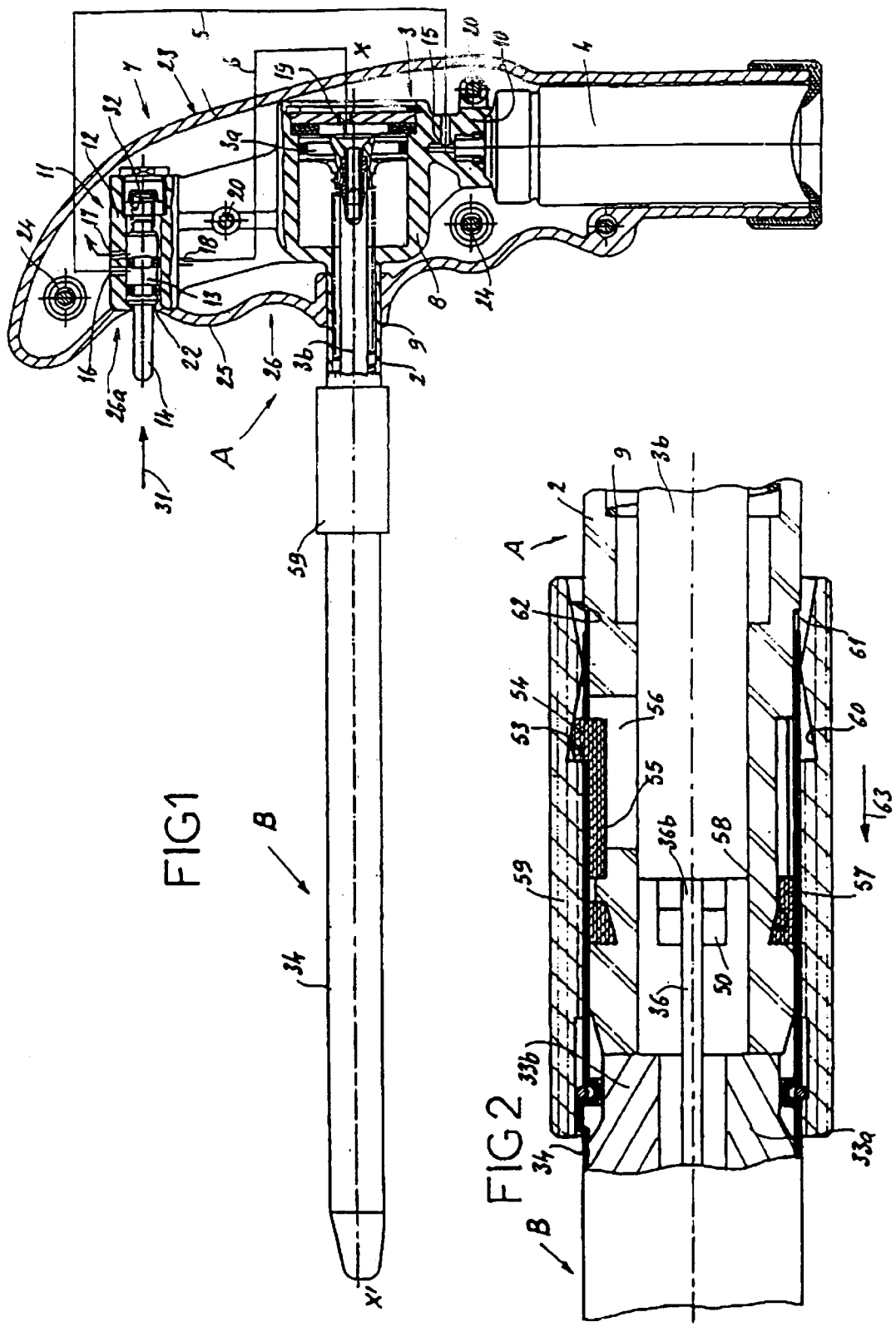

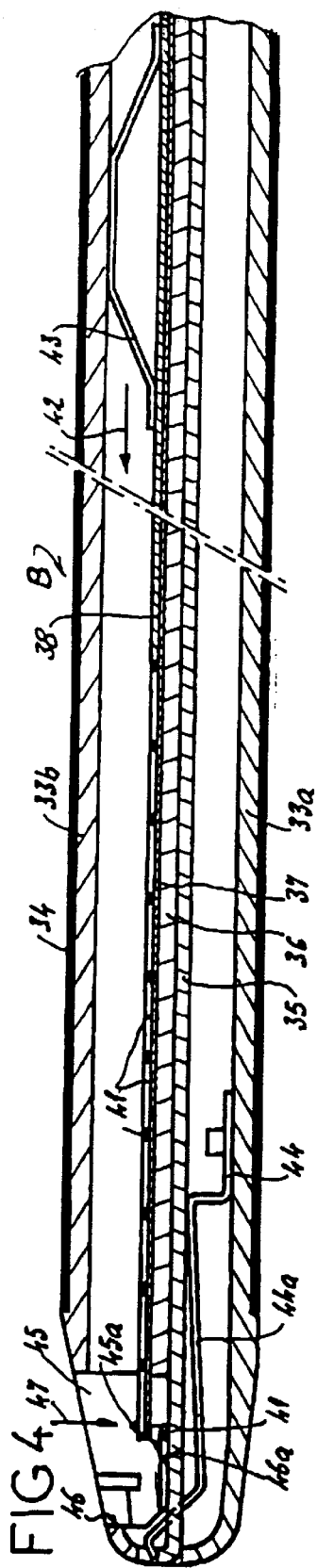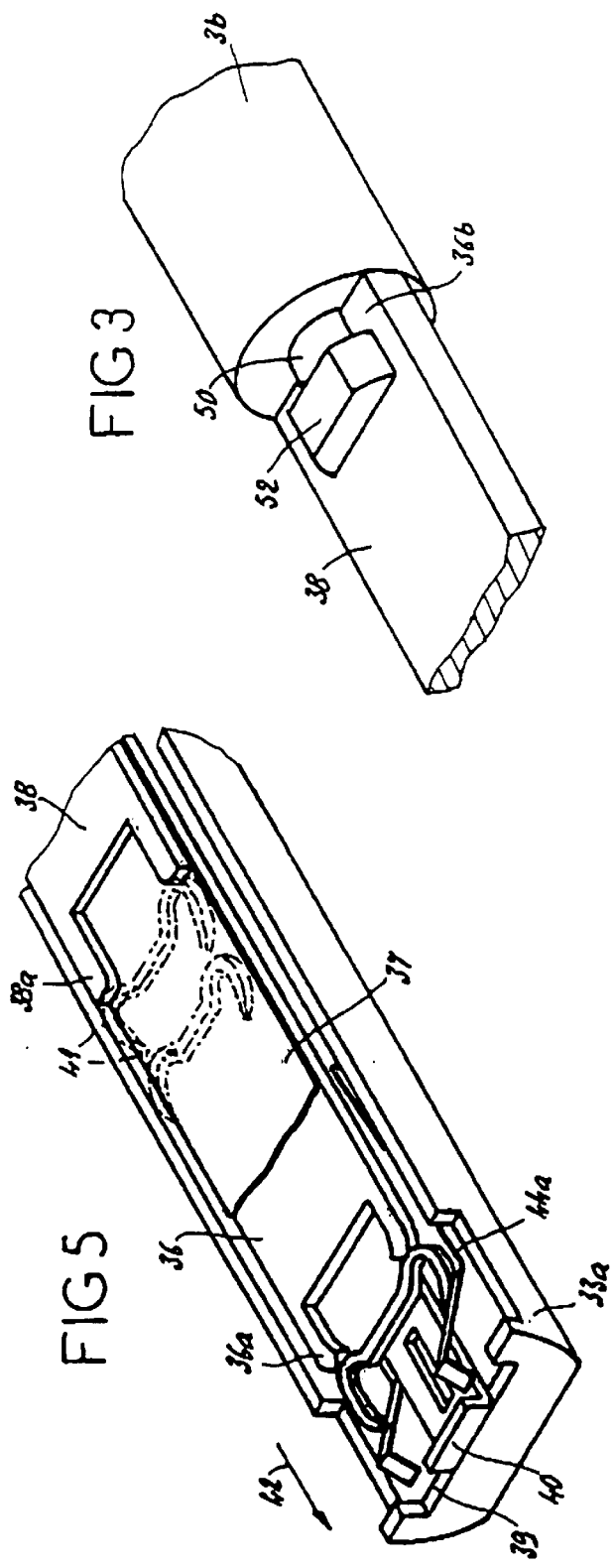

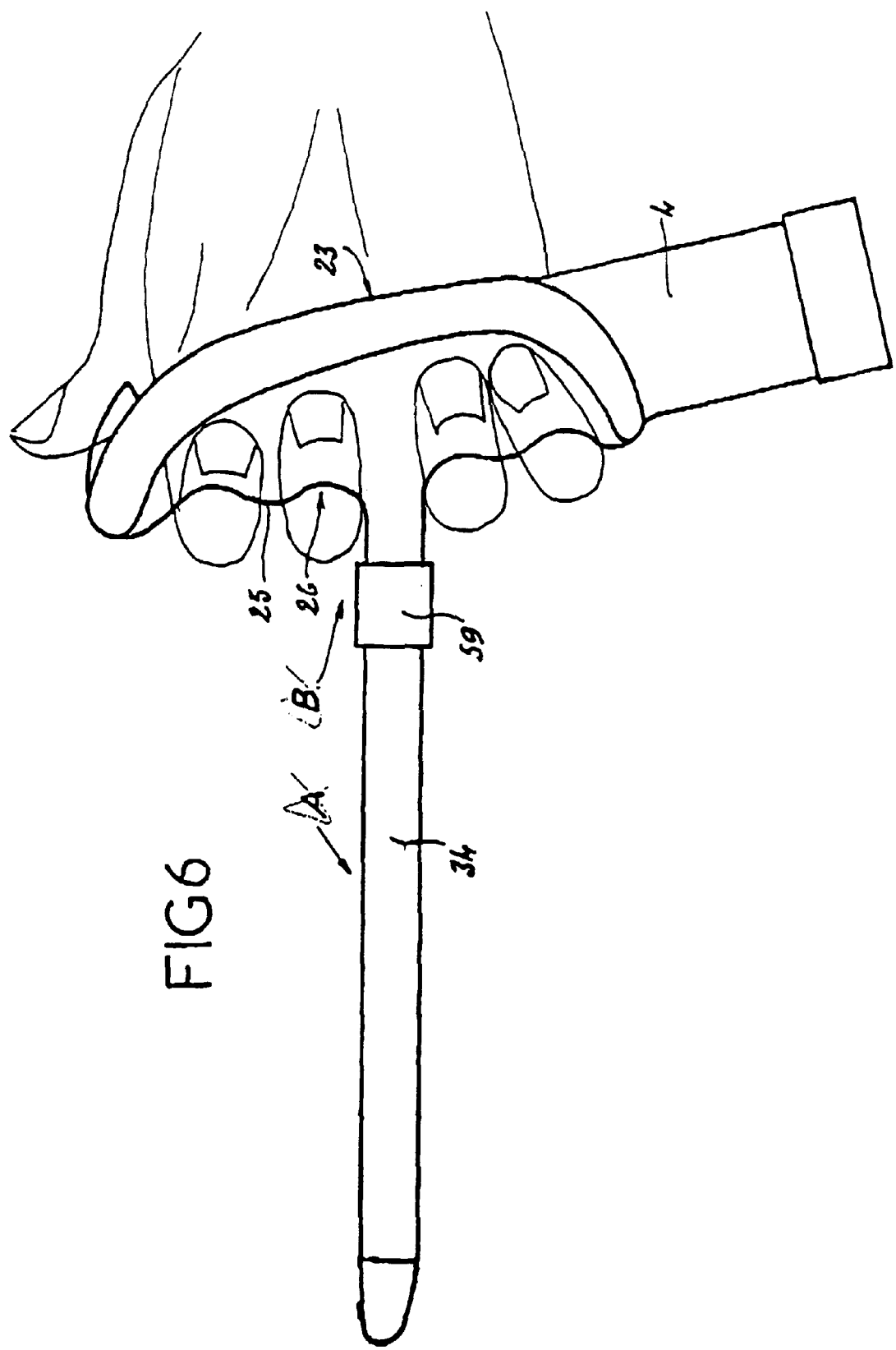

PNEUMATIC SURGICAL INSTRUMENT FOR THE DISTRIBUTION AND PLACEMENT OF CONNECTING OR FASTENING MEANS

The invention relates to a pneumatic surgical instrument for individual distribution and placement of connecting or fastening means, such as a staple, nail or anchor, or other elements of diverse forms, made of absorbable or nonabsorbable materials, used in surgery for fastening, stapling, ligaturing or joining purposes.

Staplers are known which comprise, as described in GB-A-1,328,841, EP-A-0,041,022, and more especially EP-A-0,192,418, a handle body with attachment piece on which an interchangeable terminal stapling element is joined, consisting of a magazine of staples, means for individual distribution of these staples and means for shaping and closure of a staple, the body of the handle containing a pressurized gas reservoir, a pneumatic circuit, a pneumatic thrustor, means for joining to the aforementioned distribution means, and a trigger mechanism.

In EP-A-0,192,418 and U.S. Pat. No. 4,569,469, the handle body is in the form of a pistol handle and the trigger mechanism consists of a pneumatic distributor with slide, which, arranged on a circuit extending from the gas reservoir to the actuating thrustor for the distribution means, is controlled by a push-button protruding from the handle body and on the same side as the attachment piece, like the trigger on a pistol.

In instruments of this type, the activation of the trigger mechanism by the surgeon generates reaction forces which, although slight, are multiplied by the lever arm formed between the longitudinal axis of the handle body and that of the activating push-button. The result of this is that the activation of the push-button by the surgeon generates a tilting moment tending to distance the end of the stapler, distributing the staple, from the stapling zone and thus necessitates manual checking on the part of the surgeon in order to avoid the staple being badly positioned. This disadvantage is even greater in instruments used in celioscopy since the slight displacement of the handle is amplified at the free end of the terminal element, which is in this case much longer, and leads to poor positioning of the connection or staple.

Another disadvantage of the current stapling instruments is that they are for single use only, that is to say they are discarded after use, for the reason that they cannot be correctly sterilized. The purchase price of such instruments increases the cost of the surgical intervention.

The object of the present invention is to remedy this by making available a pneumatic surgical instrument for distribution and placement of connecting or fastening means, not exerting any moment of reaction, affording precise and reliable placement, and of which at least the body can be reused after sterilization.

To this end, in the instrument according to the invention, the handle body constitutes one of the branches of a T, of which the other branch is formed by its attachment piece which is continued by the interchangeable element, and this body includes, on the side toward the interchangeable element, indentations for positioning the fingers of the hand, said indentations being arranged on either side of the attachment piece, and of which one, for positioning the index finger, is equipped with a bore through which there protrudes the push-button for activating the pneumatic distributor.

The body of the instrument has a T-shape which can be comfortably gripped in the surgeon's hand in the same way as a traditional corkscrew top, and which permits precise positioning of the end of the interchangeable element on the zone of the human body requiring stapling, ligaturing, or fastening of an external body. The activation of the push-button for triggering the operation has no effect on the position of the terminal element, first because this push-button directly activates the slide of a pneumatic distributor, causing no reaction force, and also because the force exerted by the surgeon is applied in parallel and counter to the force of application of the end of the terminal element on the operating zone and hence tends, at the very most, to reduce this application force, without modifying its direction.

The omission of any mechanical means which are polluting and difficult to sterilize, in combination with the simple and compact structure of the handle body, makes it possible for this handle body to be sterilized without any problem, and hence to be reused, thereby reducing the cost of using it, in a surgical intervention, to the purchase price of the disposable interchangeable element.

The indentations improve gripping of the handle and, by giving a constant position for each of the fingers of the hand, obliges the surgeon to adopt the same position at all times, which prevents any drift which could lead to tilting moments or to a change in the position of the end of the terminal element.

The attachment piece of the handle body is advantageously cylindrical and includes locking means able to cooperate with complementary means carried by the cylindrical body of the interchangeable element, these means being formed by longitudinal tongues mounted on the body with the possibility of radial elastic clearance, and of which one end is linked to the attachment piece, while the other end is equipped with an indentation protruding substantially radially outward, this indentation being able, on the one hand, to engage in one of the seats formed radially in the tubular body of the interchangeable element and, on the other hand, to cooperate with a frustoconical groove formed in an unlocking ring mounted so as to slide on the rear end of the body.

This method of joining between the handle body and the interchangeable terminal element makes it easier to replace this element, either for adapting its structure and the connecting or fastening means it contains to the operation which is to be performed, or for replacing it when the magazine no longer contains any connecting or fastening means, or, finally, for replacing it with an uncontaminated element, for example, for a new operation carried out reusing the handle body, after sterilization of the latter.

Other characteristics and advantages will become apparent from the following description in which reference is made to the attached diagrammatic drawing which shows, by way of example, an embodiment of this instrument when it is cooperating with a stapling element.

FIG. 1 is a side elevation of the handle body, with partial sectioning;

FIG. 2 is a partial side view showing, on an enlarged scale, the joining means between the attachment piece of the handle body and the interchangeable stapling element;

FIG. 3 is a partial perspective view showing, on an enlarged scale, the joining means between the rod of the piston of the thrustor and the rear end of the punch of the stapling element;

FIG. 4 is a side view, in longitudinal section, of the front end of the stapling element;

FIG. 5 is a partial perspective view of the lower part of the end of the stapling element;

FIG. 6 is a side elevation of the stapler when it is in the operating position.

As is shown in a general manner in FIG. 1, this pneumatic surgical instrument consists of a handle body A with an attachment piece 2 on which an interchangeable terminal element B is joined which, in this embodiment, is an element for individual distribution and placement of staples, but which can also consist of an element ensuring the same functions but for different connecting or fastening means, such as nails, anchors, ligatures, made of absorbable or nonabsorbable materials.

The body 2 contains a pneumatic single-action thrustor 3, a gas reservoir 4, a pneumatic circuit 5, 6 and a trigger mechanism, designated generally by 7.

According to the invention, the handle body A is substantially perpendicular to the longitudinal axis x'-x of its attachment piece 2 and of the interchangeable element B, giving the instrument the general shape of a T, of which one of the branches is formed by the handle body and the the other branch by the attachment piece 2, continued by the interchangeable element B.

The piston 3a of the thrustor 3 is mounted so as to slide in a thrustor body 8 which is in one piece with the attachment piece 2, in which the rod 3b of this thrustor moves freely and in which the return spring 9 of the piston 3a is accommodated. The body 8 is also in one piece with a connector 10 for securing the end of the gas reservoir 4. The longitudinal axis of this reservoir is arranged substantially perpendicular to the longitudinal axis x'-x of the instrument. The body 8 is again in one piece with the body 12 of a pneumatic distributor 11 whose slide 13 protrudes from this body in the direction of the free end of the interchangeable terminal element B in order to form a push-button 14. The longitudinal axis of the slide 13 and of the push-button 14 is parallel to the longitudinal axis x'-x of the element B.

FIG. 1 shows clearly that the connector 10 includes internal channels 15 forming a communication between the gas reservoir 4 and a conduit which, constituting the circuit 5, leads to a supply channel 16 formed in the body 12 of the distributor. This body also includes a channel 17 for escape to the atmosphere and an internal channel 18 allowing it to be connected, via a conduit constituting the circuit 6, to the supply channel 19 of the rear chamber of the thrustor 3.

The body 8 is fixed, by transverse screws 20, on at least one of the two symmetrical shells 23 enclosing it and constituting the handle body. These two shells are obtained by molding, from metal or synthetic material. They form an ergonomic handle and include, in their wall 25 directed toward the interchangeable element B, indentations 26 for positioning the fingers, and they have an opposite wall 27 which is convex so as to fit the palm of the hand. The indentation 26a, intended for positioning the index finger, is equipped with a bore 22 through which there protrudes the push-button 14 of the distributor 11 constituting the trigger mechanism of the instrument.

As is shown in FIG. 6, this handle body can be very easily gripped by the surgeon whose fingers are arranged on either side of the attachment piece 2, in the corresponding indentations 26. By means of this precise positioning, the surgeon has complete control of the position of the interchangeable element B which is in general disposed vertically or substantially vertically and in such a way that its nose comes to lie above the operating zone of the human body. When the surgeon activates the push-button, by pressing on it with the index finger, in the direction of arrow 31 (cf. FIG. 1), the compression of the return spring 32 of the slide 13 generates a very slight resistance force, which has no influence on the position of the handle or on that of the elongate element B. Likewise, using a pneumatic distributor eliminates any reaction tending to tilt the handle and guarantees almost instant triggering of the delivery of the pneumatic thrustor 3, hence of the functioning of the instrument.

Referring to FIGS. 4 and 5, we will now proceed to describe one embodiment of the interchangeable terminal element B and its function. This element is made up of a body formed by a lower shell 33a and an upper shell 33b which are enclosed in a cylindrical envelope 34. Arranged inside the body, and positioned transversely in appropriate grooves (not shown), and from the bottom upward, there are a metal blade 35, a punch 36, a separating blade 37 and a pusher 38. The blade 35 is fixed and is equipped, at its end fitting in an opening 39 formed at the end of the shell 33a, with an angled return piece 40 forming an anvil. The punch 36, which is connected via its rear end to the rod of the thrustor, as will be described in detail below, is equipped at its front end with a C-shape 36a cooperating, in a known manner, with the anvil 40 in order to deform the staples 41 arranged in the magazine. The blade 37 is fixed and, on its upper face forming the magazine, receives the staples 41 which are placed flat with their two wings turned in the direction of the end of the magazine. The pusher 38 is applied to the separating blade 37 and is subjected permanently to the action of spring means which tend to push the staples 41 in the direction of the arrow 42. A spring 43 lays this pusher against the blade 37. FIG. 5 shows that the front end 38a of the pusher 38 is also a C shape in order to come into contact, in a localized manner, with the staples 41. An extraction spring 44, fixed on the bottom of the lower shell 33a, includes two parallel blades 44a extending on either side of the anvil 40 and normally lying in the trajectory of each of the branches of a staple 41.

This stapling device is completed by a wedge 45 mounted so as to slide vertically in a recess 46 formed in the upper half shell 33b'. This wedge is permanently subject to elastic return means tending to lay it against the blade 35, that is to say in the direction of arrow 47 in FIG. 4. This wedge includes an abutment face 45a countering the displacement of the staples, in the direction of arrow 42, and a sloping face 46a disposed in the trajectory of the punch 36.

When the pneumatic thrustor 3 is charged, it provokes the displacement of the punch 36 in the direction of the arrow 42. The front end of the punch 36 thus comes into contact against the sloping face 46a of the wedge 45 and causes this wedge to lift. Simultaneously, the punch comes into contact with the staple 41 lying on the blade 35, under the wedge, and brought beforehand into this positon. As is shown in FIG. 5, during the displacement of the staple 41 by the punch 36, the branches of the staple 41 come to bear on the spring leaves 44 and push them downward, and the transverse branch of this staple comes to bear against the anvil 40. In a known manner, the continuation of the movement of the pusher 36, in the direction of arrow 42, allows the end 36a of this pusher, whose branches bear on the branches of the staple, to close the branches of this staple, ensuring stapling. During the return of the pusher, ensured by the return spring 9 of the piston of the pneumatic thrustor 3, the spring leaves 44 lift the transverse branch of the staple 41 and pass it over the anvil 40, thereby releasing the stapling element B. During the withdrawal of the punch 36, and before the wedge 45 comes back to its position in which it blocks the magazine of staples, the frontmost staple 41 drops onto the blade 35 in readiness for the next stapling.

Referring to FIGS. 1, 2 and 3, we will now proceed to describe the joining means between the handle A and the terminal element B permitting the interchangeability of this element B. FIG. 3 shows that the rear end of the punch 36 is equipped with a cover 3b, of C-shape, intended to cooperate with a T-shaped catch 50 formed at the front end of the rod 3b of the piston. This catch is equipped with two opposite flats 52 which permit fastening of the cover 36b on this catch by relative rotation, through 90°, of one or other of these elements about their longitudinal axis.

FIG. 2 shows that the cylindrical envelope 34 of the interchangeable element B includes one or more recesses 53 which are positioned angularly in a diameteral plane of the body and in relation to the punch 36 in such a way as to come into line with the locking indentations 54, projecting radially outward, only when the C-shaped cover 36b of the punch engages over the catch 50 of the rod 3b of the piston. Each indentation 54 is formed at the end of an elastically deformable tongue 55 arranged longitudinally on the cylindrical attachment piece 2, at least partly in a radial recess 56 permitting its clearance. In the embodiment shown, this tongue is integral with a ring 57 fitted elastically in a groove 58 of the attachment piece 2.

By virtue of this arrangement, fitting an interchangeable element on the attachment piece 2 is done by positioning the element B angularly in such a way that it is pivoted through 90° in relation to its normal operating position, then by fitting its cylindrical outer envelope 34 on the cylindrical attachment piece 2 until this envelope abuts on a shoulder 61 of the attachment piece. Thereafter, rotation of the element B, bringing it back to its normal operating position, simultaneously ensures, on the one hand, the joining by engagement between the punch 36 and the rod 3b of the piston, and, on the other hand, the engagement of the indentations 54 in the recesses 53.

The unlocking of the indentations, which is necessary for proceeding with the reverse operation with a view to disconnecting the element B from the handle A, is ensured by a ring 59, mounted so as to slide longitudinally at the end of each cylindrical envelope 34. This ring includes a frustoconical groove 60 preceded by a inverted conical bevel 62. When the ring is displaced in the direction of arrow 63, the biconical groove forces the indentation or indentations 54 inward, thereby allowing the corresponding recesses 53 to escape these indentations. During engagement of the ring 59 on the attachment piece 2, the conical bevel 62 makes it possible to push the indentations 54 aside before they come into contact with the end of the envelope 34.

This joining device is very simple to use and permits practically instant assembly and disassemby of the terminal element B on the handle body A.

It will be apparent from the above that compared to the current pneumatic surgical staplers, the instrument according to the invention has an ergonomic handle with direct activation eliminating any incorrect positioning of the hand, any tilting moment upon its activation, and hence guaranteeing precise positioning of its nose in relation to the operating zone. Moreover, the simplification of the body A allows it to be sterilized for re-use with another disposable terminal element, identical to the preceding one or different in terms of its length, of the connecting or fastening means contained in its magazine, and of the means of distribution and placement adapted to these means.

What is claimed is:

1. A pneumatic surgical instrument for distribution and placement of connectors or fasteners, the instrument comprising:
   a) a handle body integral with an attachment piece;
   b) an interchangeable terminal element joined and fixed to the attachment piece in a removable manner;
   c) said interchangeable terminal element forming a magazine for the connectors or fasteners;
   d) the terminal element also containing a distributor that can individually distribute the connectors or fasteners;
   e) a means for placement of each connector or fastener;
   f) the body of the handle, being substantially perpendicular to an axis of its attachment piece, and containing a pressurized gas reservoir;
   g) a pneumatic thrustor with single action and a spring return for activating the distributor and the placement means;
   h) a pneumatic circuit extending from the reservoir to the thrustor;
   i) a pneumatic distributor arranged on the pneumatic circuit;
   j) a push-button to activate the distributor, wherein said push-button protrudes from the handle body on the same side of the handle body as the attachment piece;
   k) wherein the handle body constitutes a first of two branches of a T, and wherein a second branch of the T is formed by the attachment piece which is continued by the interchangeable element;
   l) indentations included on the handle body, the indentations being provided to position fingers of a hand, said indentations being arranged along the handle body on either side of the attachment piece;
   m) one of the indentations being an index finger indentation, for positioning an index finger; and
   n) the index finger indentation being equipped with a bore having the push-button protruding through the bore to activate the pneumatic distributor.

2. The surgical instrument of claim 1, further comprising:
   a) a body of the thrustor being in one piece; and
   b) the thrustor including a connector for fastening the gas reservoir.

3. The surgical instrument of claim 1, further comprising:
   a) a body of the thrustor being in one piece; and
   b) a body of the distributor, and its longitudinal axis having the attachment piece, that can join with the interchangeable element to imprison the body of the thrustor within conduits, of the pneumatic circuit between two shells that make up the handle body.

4. The surgical instrument of claim 1, wherein the attachment piece of the handle body is cylindrically shaped, and includes a locking means that cooperates with a complimentary means carried by a cylindrical body of the interchangeable element.

5. The surgical instrument of claim 4, wherein the locking means is formed by longitudinal tongues mounted on the cylindrical body of the interchangeable element, with a possibility of radical elastic clearance, and wherein one end of the locking means is linked to the attachment piece, while the other end of the locking means includes an indentation protruding substantially radially outward.

6. The surgical instrument of claim 5, wherein the indentation can engage with a complimentary means formed radially in the tubular body of the interchangeable element, and wherein the indentation is also able to cooperate with a frustoconical groove formed in an unlocking ring mounted so that the ring can slide on the rear end of the body of the interchangeable element.

7. The surgical instrument of claim 1, wherein a rod of a piston is equipped, at its rear end fitting into the attachment piece, with a T-shaped catch that comprises two flats positioned opposite each other so that the flats can be engaged by a C-shaped cover located at the rear end of a punch included in the interchangeable element.

8. The surgical instrument of claim 7, wherein the engagement between the T-shaped catch and the C-shaped cover is achieved by a relative rotation of 90° between the interchangeable element and the attachment piece of the handle body.

9. The surgical instrument of claim 4, wherein a rod of a piston of the thrustor is equipped, at its rear end fitting in the attachment piece, with a T-shaped catch comprising two flats positioned opposite each other so that the flats can be engaged by a C-shaped cover formed at the rear end of a punch that is displaceable in the interchangeable element, this engagement being achieved by relative rotation of 90° between the interchangeable element and the attachment piece of the handle body, and wherein the complimentary means are seats that are formed in the cylindrical body of the interchangeable element and are positioned angularly in a diametral plane of the body of the interchangeable element and in relation to punch indentations only when the C-shaped cover of the punch engages over the T-shaped catch of the piston.

* * * * *